United States Patent
Stevens et al.

(10) Patent No.: US 9,360,343 B2
(45) Date of Patent: Jun. 7, 2016

(54) MONITORING USE OF A SINGLE ARM WALKING AID

(75) Inventors: Mark B. Stevens, Austin, TX (US); John D. Wilson, Houston, TX (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 991 days.

(21) Appl. No.: 13/532,224

(22) Filed: Jun. 25, 2012

(65) Prior Publication Data

US 2013/0346021 A1    Dec. 26, 2013

(51) Int. Cl.
*G01C 22/00* (2006.01)
*A61B 5/11* (2006.01)
*G06F 19/00* (2011.01)
*A61B 5/00* (2006.01)
*A45B 3/00* (2006.01)
*A45B 9/00* (2006.01)
*A61H 3/02* (2006.01)
*G08B 21/04* (2006.01)
*A61B 5/103* (2006.01)

(52) U.S. Cl.
CPC ............ *G01C 22/006* (2013.01); *A45B 3/00* (2013.01); *A45B 9/00* (2013.01); *A61B 5/11* (2013.01); *A61B 5/112* (2013.01); *A61B 5/486* (2013.01); *A61B 5/7455* (2013.01); *G06F 19/3481* (2013.01); *A61B 5/0004* (2013.01); *A61B 5/1038* (2013.01); *A61B 2562/0219* (2013.01); *A61B 2562/0247* (2013.01); *A61B 2562/0257* (2013.01); *A61H 3/02* (2013.01); *A61H 2201/5012* (2013.01); *A61H 2201/5064* (2013.01); *G08B 21/0446* (2013.01)

(58) Field of Classification Search
CPC .......... G01C 22/006; A45B 3/00; A61B 5/00; A61B 5/11; A61B 5/112
USPC .................................................. 702/150, 160
See application file for complete search history.

(56) References Cited

U.S. PATENT DOCUMENTS

| | | | |
|---|---|---|---|
| 4,858,125 A | 8/1989 | Washizuka et al. |
| 5,511,571 A | 4/1996 | Adrezin et al. |
| 5,885,229 A | 3/1999 | Yamato et al. |
| 6,011,481 A | 1/2000 | Luther et al. |
| 6,234,982 B1 | 5/2001 | Aruin |
| 7,346,396 B2 | 3/2008 | Barriskill et al. |
| 7,385,514 B2 | 6/2008 | Dempsey |
| 7,778,112 B2 | 8/2010 | Behm et al. |

(Continued)

OTHER PUBLICATIONS

Strausser et al., "The Development and Testing of a Human Machine Interface for a Mobile Medical Exoskeleton", Sep. 25-30, 2011, IEEE Internatinal Conference on Intelligent Robots and Systems, pp. 4911-4916.*

(Continued)

*Primary Examiner* — John Breene
*Assistant Examiner* — Yaritza H Perez Bermudez
(74) *Attorney, Agent, or Firm* — Paul S. Drake

(57) ABSTRACT

A method, system or computer usable program product for monitoring single arm walking aid use of a user including providing a sensor on at least one of a left shoe, a right shoe and a single arm walking aid, using the sensor, determining a relative position of a set of footsteps by a left foot, a set of footsteps by a right foot, and a set of placements of the single arm walking aid, and using the relative position data, determining whether the user is practicing correct single arm walking aid use.

20 Claims, 8 Drawing Sheets

(56) References Cited

U.S. PATENT DOCUMENTS

| | | | |
|---|---|---|---|
| 7,826,983 | B2 | 11/2010 | Alwan et al. |
| 7,836,904 | B1 | 11/2010 | Cushman |
| 2002/0143491 | A1* | 10/2002 | Scherzinger ............... 702/160 |
| 2004/0015207 | A1* | 1/2004 | Barriskill et al. ............ 607/49 |
| 2008/0072940 | A1* | 3/2008 | Cheng et al. ............... 135/66 |
| 2008/0191864 | A1* | 8/2008 | Wolfson ..................... 340/524 |
| 2009/0260426 | A1* | 10/2009 | Lieberman et al. ......... 73/65.01 |
| 2010/0049095 | A1 | 2/2010 | Bunn et al. |
| 2010/0063779 | A1* | 3/2010 | Schrock et al. ............ 702/188 |
| 2010/0274304 | A1 | 10/2010 | Wang et al. |
| 2011/0061697 | A1 | 3/2011 | Behrenbruch et al. |
| 2011/0119027 | A1* | 5/2011 | Zhu et al. .................... 702/160 |
| 2013/0231595 | A1* | 9/2013 | Zoss et al. ................... 601/34 |
| 2013/0237884 | A1* | 9/2013 | Kazerooni et al. .......... 601/34 |

OTHER PUBLICATIONS

K. Strausser, "Developement of a Human Machine Interface for a Wearable Interface for a Wearable Exoskeleton for Users with Spinal Cord injury", 2011, pp. 1-102.*

Au et al, "Active Guidance Towards Proper Cane Usage", Proceedings of the 5th International Workshop on Wearable and Implantable Body Sensor Networks, The Chinese University of Hong Kong, China, pp. 205-208, Jun. 1-3, 2008.

Wu et al, "The SmartCane System: An Assistive Device for Geriatrics", under grants NLM T15 LM07356 and ANI-00331481, BodyNets08, 2008.

"The GAITRite Portable Walkway System", CIR Systems, Inc., 2010, published on the world wide web at: www.gaitrite.com/Downloads/GAITRite.ppt.

"My Gillette Visit", Gillette Children's Specialty Healthcare, published on the world wide web at: www.gillettechildrens.org/default.cfm?PID=1.6.14.2.

"Gait Monitor Watches for Decline in Walking as Folks Age", Medgadget.com, 2009, published on the world wide web at: http://medgadget.com/2009/04/gait_monitor_watches_for_decline_in_walking_as_folks_age.html.

"Enhance Gait Analysis with Pressure Mapping", Tekscan, Inc., published on the world wide web at: http://www.tekscan.com/medical/gait-analysis.html.

Woodbridge et al, "Wireless Health and the Smart Phone Conundrum", UCLA, published on the world wide web at: www.cs.ucla.edu/~ani/publications/smartphoneconundrum.pdf.

"U.Va.'s Institute on Aging Teams University Researchers with Health Care Technology Company to Develop Novel Sensor Devices for the Elderly", University of Virginia, Apr. 13, 2009, published on the world wide web at: www.virginia.edu/uvatoday/newsRelease.php?id=8301.

* cited by examiner

MONITORING USE OF A SINGLE ARM WALKING AID

BACKGROUND

1. Technical Field

The present invention relates generally to monitoring the use of a single arm walking aid, and in particular, to a computer implemented method for monitoring a person's use and gait when using a single arm walking aid.

2. Description of Related Art

Persons with limited mobility may be provided or acquire a walking aid such as a walker, cane, crutches, etc. The walking aid is used to allow the user to move about while helping prevent falls which can cause further injuries. The walking aid also relieves pressure on various parts of the body depending on the type of walking aid used and how the walking aid is used. This may help prevent additional stress and injury to those parts of the body as well as allow those parts of the body to heal.

If the limited mobility is primarily to one side of the body, then a single arm walking aid may be used such as a cane or a single crutch. The limited mobility may be caused by an injury, arthritis, or other malady to a foot, leg, hip or lower back on one side of a user. The cane or single crutch can help reduce weight and pressure from the injured body part and assist with balance while the user is walking or otherwise moving about. The helps the user to safely retain mobility while relieving stress and allowing any injured body part to heal.

SUMMARY

The illustrative embodiments provide a method, system, and computer usable program product for monitoring single arm walking aid use of a user including providing a sensor on at least one of a left shoe, a right shoe and a single arm walking aid, using the sensor, determining a relative position of a set of footsteps by a left foot, a set of footsteps by a right foot, and a set of placements of the single arm walking aid, and using the relative position, determining whether the user is practicing correct single arm walking aid use.

BRIEF DESCRIPTION OF THE SEVERAL VIEWS OF THE DRAWINGS

The novel features believed characteristic of the invention are set forth in the appended claims. The invention itself, further objectives and advantages thereof, as well as a preferred mode of use, will best be understood by reference to the following detailed description of illustrative embodiments when read in conjunction with the accompanying drawings, wherein:

DETAILED DESCRIPTION

Steps may be taken to monitor the use of a single arm walking aid. These steps may be taken as will be explained with reference to the various embodiments below.

Figure 1:
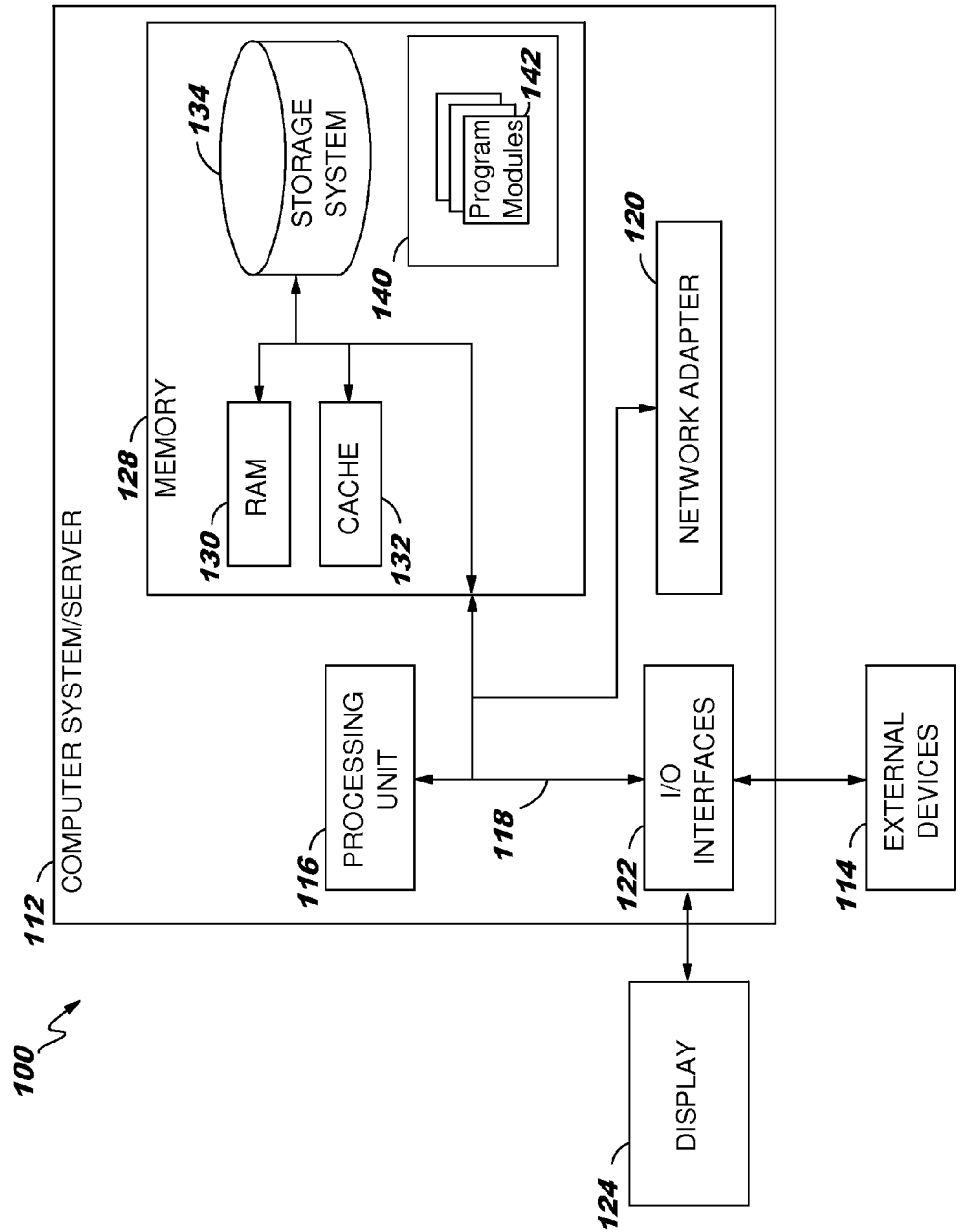
FIG. 1 is a block diagram of a data processing system in which various embodiments may be implemented.

FIG. 1 is a block diagram of a data processing system in which various embodiments may be implemented. Data processing system 100 is only one example of a suitable data processing system and is not intended to suggest any limitation as to the scope of use or functionality of embodiments of the invention described herein. Regardless, data processing system 100 is capable of being implemented and/or performing any of the functionality set forth herein.

In data processing system 100 there is a computer system/server 112, which is operational with numerous other general purpose or special purpose computing system environments, peripherals, or configurations. Examples of well-known computing systems, environments, and/or configurations that may be suitable for use with computer system/server 112 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 112 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 112 may be practiced in distributed computing environments where tasks are performed by remote processing devices that are linked through a communications network. In a distributed computing environment, program modules may be located in both local and remote computer system storage media including memory storage devices.

As shown in FIG. 1, computer system/server 112 in data processing system 100 is shown in the form of a general-purpose computing device. The components of computer system/server 112 may include, but are not limited to, one or more processors or processing units 116, a system memory 128, and a bus 118 that couples various system components including system memory 128 to processor 116.

Bus 118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 112 typically includes a variety of computer system readable media. Such media may be any available media that is accessible by computer system/server 112, and it includes both volatile and non-volatile media, removable and non-removable media.

System memory 128 can include computer system readable media in the form of volatile memory, such as random access memory (RAM) 130 and/or cache memory 132. Computer system/server 112 may further include other removable/non-removable, volatile/non-volatile computer system storage media. By way of example only, storage system 134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 118 by one or more data media interfaces. Memory 128 may include at least one program product having a set (e.g., at least one) of program modules that are configured to carry out the functions of embodiments of the invention. Memory 128 may also include data that will be processed by a program product.

Program/utility 140, having a set (at least one) of program modules 142, may be stored in memory 128 by way of example, and not limitation, as well as an operating system, one or more application programs, other program modules, and program data. Each of the operating system, one or more application programs, other program modules, and program data or some combination thereof, may include an implementation of a networking environment. Program modules 142 generally carry out the functions and/or methodologies of embodiments of the invention. For example, a program module may be software for monitoring the use of a single arm walking aid.

Computer system/server 112 may also communicate with one or more external devices 114 such as a keyboard, a pointing device, a display 124, etc.; one or more devices that enable a user to interact with computer system/server 112; and/or any devices (e.g., network card, modem, etc.) that enable computer system/server 112 to communicate with one or more other computing devices. Such communication can occur via I/O interfaces 122 through wired connections or wireless connections. Still yet, computer system/server 112 can communicate with one or more networks such as a local area network (LAN), a general wide area network (WAN), and/or a public network (e.g., the Internet) via network adapter 120. As depicted, network adapter 120 communicates with the other components of computer system/server 112 via bus 118. It should be understood that although not shown, other hardware and/or software components could be used in conjunction with computer system/server 112. Examples, include, but are not limited to: microcode, device drivers, redundant processing units, external disk drive arrays, RAID systems, tape drives, and data archival storage systems, etc.

Figure 2:
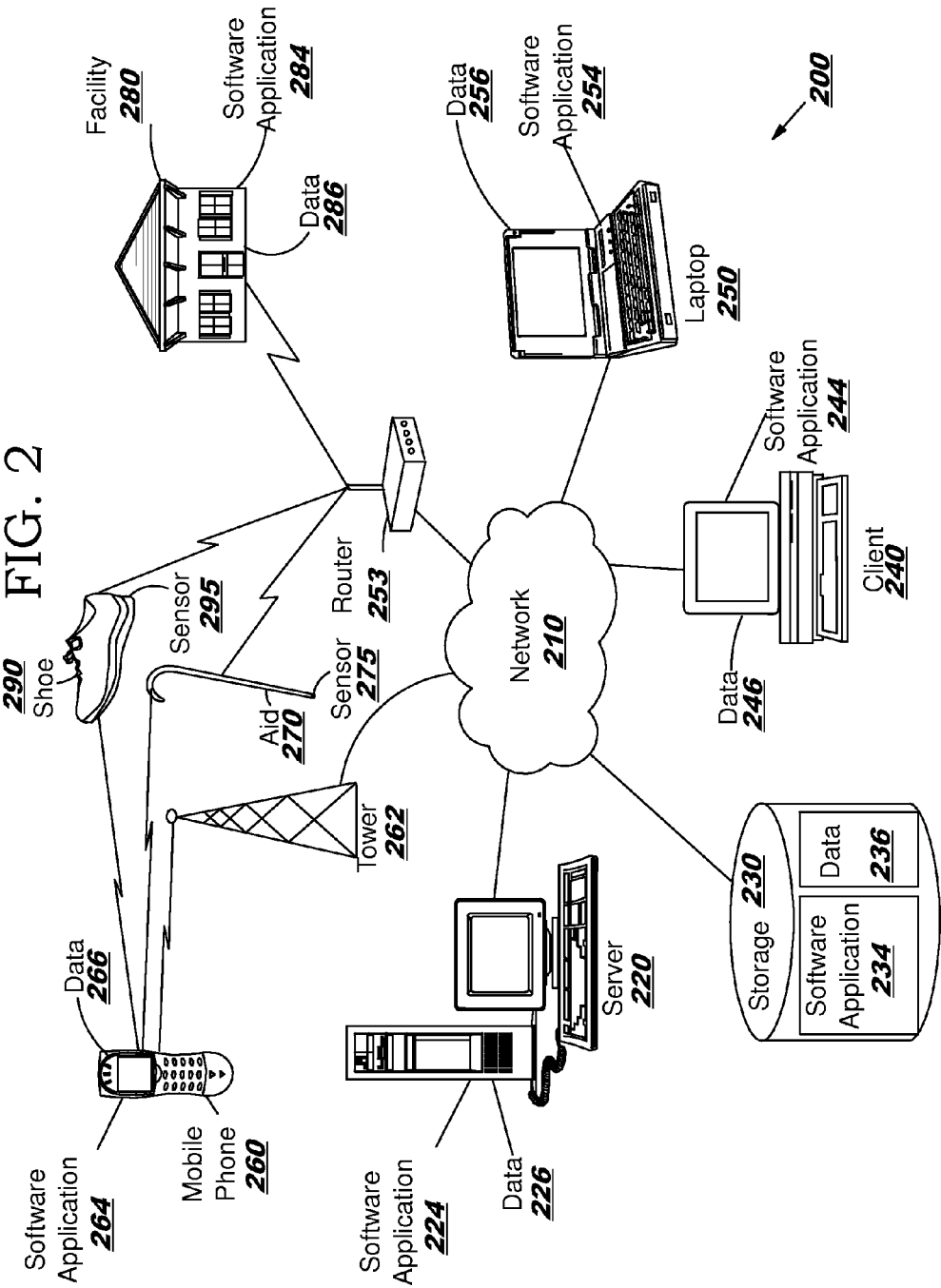
FIG. 2 is a block diagram of a network of data processing systems in which various embodiments may be implemented.

FIG. 2 is a block diagram of a network of data processing systems in which various embodiments may be implemented. Data processing environment 200 is a network of data processing systems such as described above with reference to FIG. 1. Software applications may execute on any computer or other type of data processing system in data processing environment 200. Data processing environment 200 includes network 210. Network 210 is the medium used to provide simplex, half duplex and/or full duplex communications links between various devices and computers connected together within data processing environment 200. Network 210 may include connections such as wire, wireless communication links, or fiber optic cables.

Server 220 and client 240 are coupled to network 210 along with storage unit 230. In addition, laptop 250, aid (or crutch or other single arm walking aid) 270, facility 280 (such as a home or business) and shoe 290 may be coupled to network 210 including wirelessly such as through a network router 253. A mobile phone 260 may be coupled to network 210 through a mobile phone tower 262. Data processing systems, such as server 220, client 240, laptop 250, mobile phone 260, aid 270, facility 280 and shoe 290 may contain data and have software applications including software tools executing thereon. Other types of data processing systems such as personal digital assistants (PDAs), smartphones, tablets and netbooks may be coupled to network 210.

Server 220 may include software application 224 and data 226 for monitoring the use of a cane or other single arm walking aid or other software applications and data in accordance with embodiments described herein. Storage 230 may contain software application 234 and a content source such as data 236 for monitoring the use of a single arm walking aid. Other software and content may be stored on storage 230 for sharing among various computer or other data processing devices. Client 240 may include software application 244 and data 246. Laptop 250 and mobile phone 260 may also include software applications 254 and 264 and data 256 and 266. Facility 280 may include software applications 284 and data 286. Other types of data processing systems coupled to network 210 may also include software applications. Software applications could include a web browser, email, or other software application that can monitor the use of a single arm walking aid.

Server 220, storage unit 230, client 240, laptop 250, mobile phone 260, aid 270, facility 280 and shoe 290 and other data processing devices may couple to network 210 using wired connections, wireless communication protocols, or other suitable data connectivity. Client 240 may be, for example, a personal computer or a network computer. Aid 270 and shoe 290 may be connected wirelessly to each other or to mobile phone 260 such as by near field communications such as Bluetooth and Wi-Fi. Aid 270 and shoe 290 may communicate across network 210 through router 253 or through the mobile phone. Aid 270 and shoe 290 may include sensors 275 and 295 respectively which generate information to be communicated with each other, to mobile phone 260, or across network 210.

In the depicted example, server 220 may provide data, such as boot files, operating system images, and applications to client 240 and laptop 250. Server 220 may be a single computer system or a set of multiple computer systems working together to provide services in a client server environment. Client 240 and laptop 250 may be clients to server 220 in this example. Client 240, laptop 250, mobile phone 260, Aid 270, facility 280 and shoe 290 or some combination thereof, may include their own data, boot files, operating system images, and applications. Data processing environment 200 may include additional servers, clients, and other devices that are not shown.

In the depicted example, data processing environment 200 may be the Internet. Network 210 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 2 is intended as an example, and not as an architectural limitation for the different illustrative embodiments.

Among other uses, data processing environment 200 may be used for implementing a client server environment in which the embodiments may be implemented. A client server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications.

Figure 3:
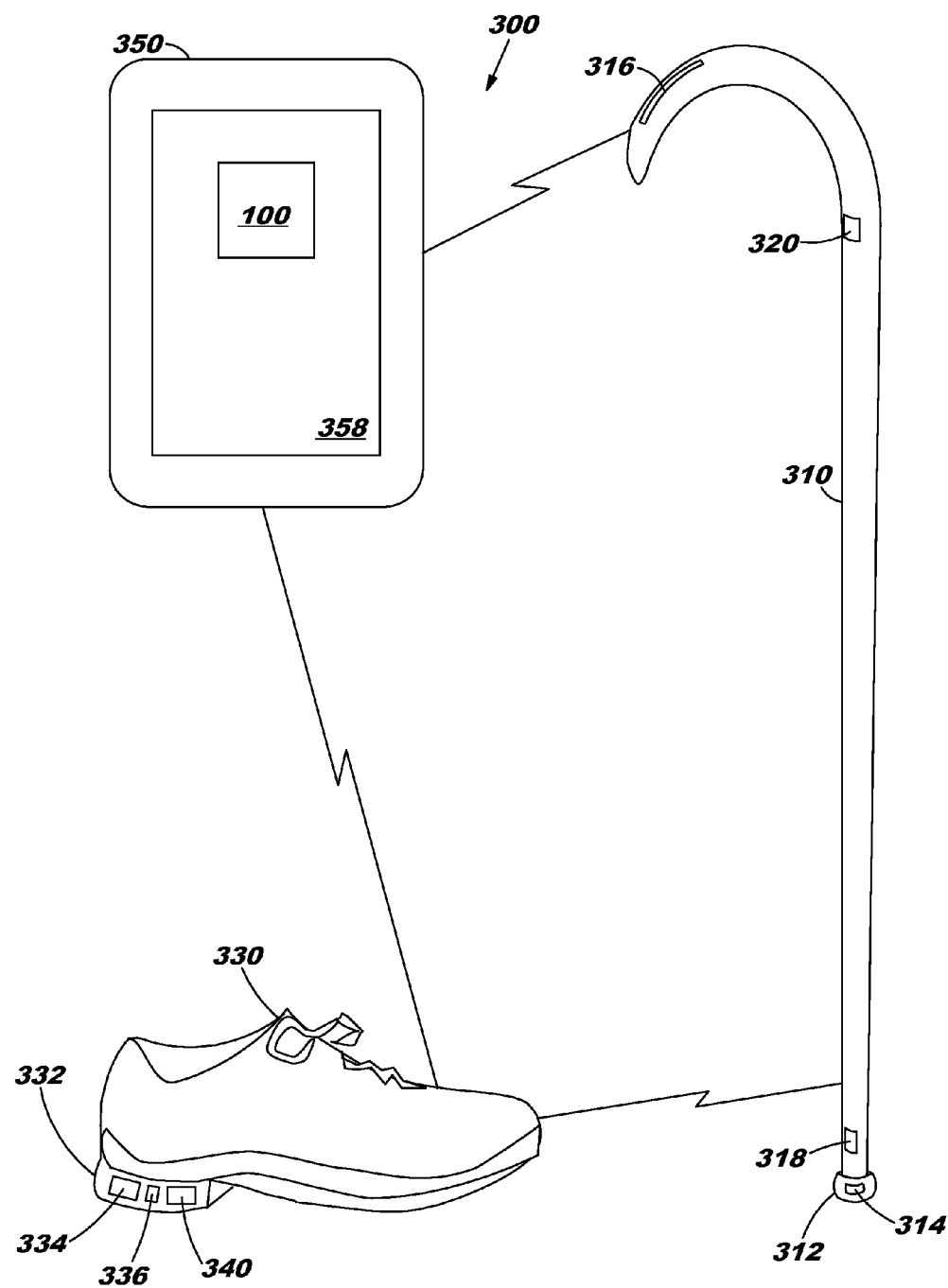
FIG. 3 is a diagram of a system for monitoring the use of a single arm walking aid by a user in which various embodiments may be implemented.

FIG. 3 is a diagram of a system for monitoring the use of a single arm walking aid by a user in which various embodiments may be implemented. This system 300 may include a single arm walking aid 300 (e.g. a cane or crutch) communicating with a shoe 330 and a mobile phone 350. The communications between these elements may be through near field communications such as Bluetooth or Wi-Fi. Other types of near field communications may be utilized such as infrared, optical, sonic or other methods. Each of these elements may also communicate with other data processing systems such as through a router or through various types of near field communications. These elements are shown for illustrative purposes, although alternative elements may be utilized such as described below.

Aid 310 may also be a cane or a crutch or other similar single arm walking aid also referred to herein as an aid or a walking aid. Aid 310 includes a pressure sensor 312 for detecting whether any pressure is being applied to the aid and may also detect the amount of pressure being applied to the aid. The pressure sensor may be piezoelectric, capacitive, electromagnetic, optical or other type of sensor for detecting force applied to the base of the aid. An accelerometer 314 or other type of motion detector may be used near the tip of the aid to detect movement of the aid. The accelerometer may be piezoelectric, capacitive, electromechanical, optical or other type of sensor for detecting acceleration. A feedback device 316 may be used to provide feedback to the user. The feedback device may be a vibrator, a light emitter, or other type of signaling device. A proximity component 318 such as a proximity detector may also be included for detecting the relative location of the shoe. The proximity detector may be a light detector, a proximity signal detector, or other type of detector. Elements 312, 314, 316 and 318 are collectively referred to herein as a module. Coupled to this module is a data processing system 320 which may be as described above with reference to FIG. 1 such as a processing unit, a memory, input and output interfaces, communication devices such as near field communication devices, etc. Alternative embodiments may use simple hardware sufficient to perform the various tasks as described below such a detecting motion, pressure, signaling or otherwise communicating with the user or other devices, etc.

Shoe 330 may also be a strap on attachment to a foot or ankle or other single foot device. Although a single shoe is shown, a second shoe may also be utilized with the same or similar elements. Shoe 330 includes a module 332 incorporated with the shoe such as by being built into the shoe or by being attached to the shoe or attached to the ankle of the user above the shoe. Module 332 includes a pressure sensor 334 for detecting whether any pressure is being applied to the base of the shoe and may also detect the amount of pressure being applied to the base of the shoe. The pressure sensor may be piezoelectric, capacitive, electromagnetic, optical or other type of sensor for detecting force applied to the base of the shoe. An accelerometer or other type of motion detector may be used near the base of the shoe to detect movement of the shoe. The accelerometer may be piezoelectric, capacitive, electromechanical, optical or other type of sensor for detecting acceleration. A proximity component 336 such as a proximity emitter may be used to provide relative location information to the aid. The signaling device may be a light emitter, a proximity emitter, or other type of signaling device. Coupled to this module is a data processing system 340 which may be as described above with reference to FIG. 1 such as a processing unit, a memory, input and output interfaces, communication devices such as near field communication devices, etc. Alternative embodiments may use simple hardware sufficient to perform the various tasks as described below such a detecting motion, pressure, signaling or otherwise communicating with other devices, etc.

One or more shoe modules and a single arm module may be collectively referred to herein as a sensor. That is, collectively they sense the relative position and timing of the strikes and releases of the footsteps and placement of the walking aid.

Mobile phone 350 may also be a laptop, a desktop or other data processing system. The use of mobile phone or its alternatives is optional as the system may be implemented with the aid and shoe alone. Mobile phone 350 includes a display 358 for communicating with the user or a medical professional through a user interface. Mobile phone 350 includes a data processing system which may be as described above with reference to FIG. 1 such as a processing unit, a memory, input and out interfaces, etc.

Figure 4:
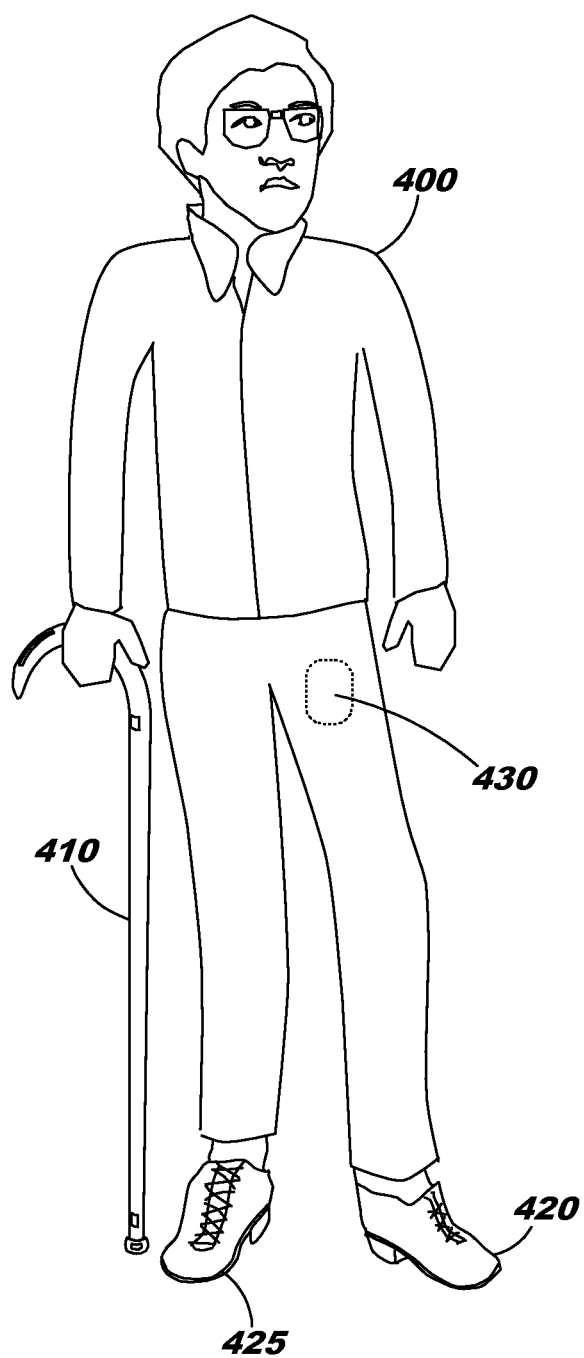
FIG. 4 is a diagram of a person using the monitoring system of FIG. 3 in which various embodiments may be implemented.

FIG. 4 is a diagram of a person using the monitoring system of FIG. 3 in which various embodiments may be implemented. In this example, the user 400 is injured in his or her left leg, so an aid 410 such as a can or crutch is held in the user's right hand. A shoe 420 with various individual sensors as described above is on the left foot, although a similar shoe 425 may also be on the right foot. An optional mobile phone 430 is located in the user's pants pocket, although it could be located elsewhere on the person. The shoe may also be a strap or other device attached to the left and or right shoe, and the optional mobile phone may be another type of data processing system.

Figure 5A:
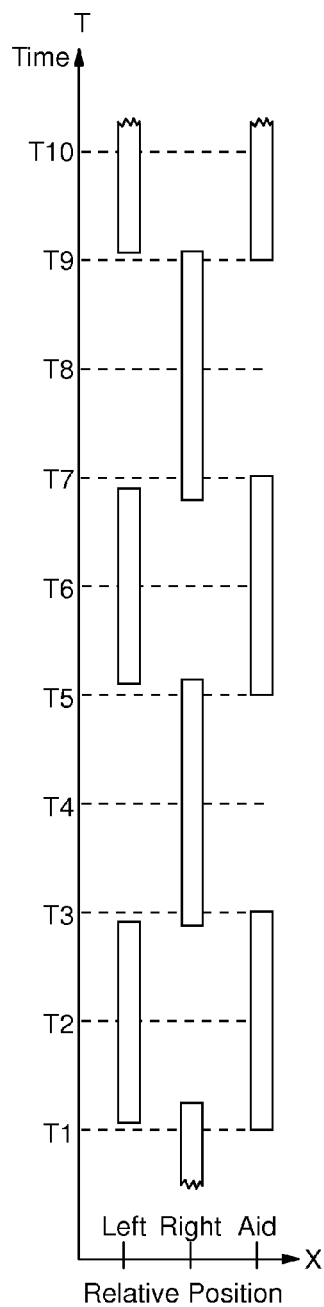
FIG. 5A through 5C illustrate proper and improper usage of a single arm walking aid in accordance with a first embodiment.
Figure 5B:
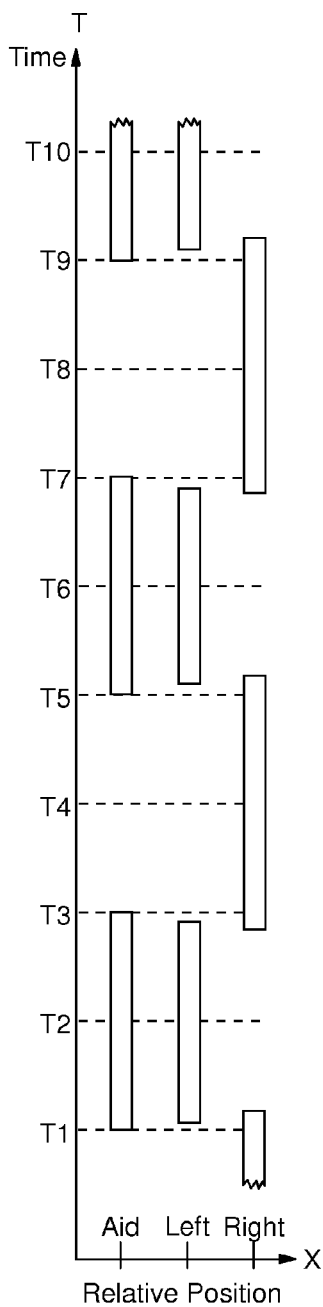
Figure 5C:
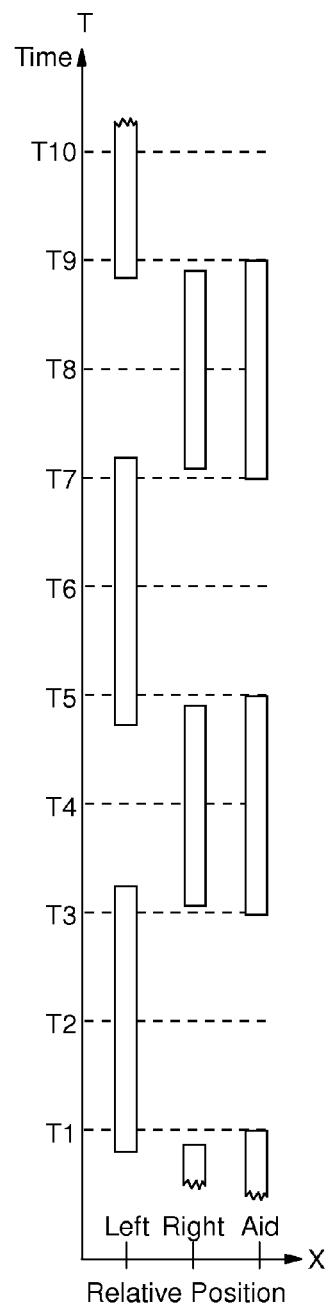

FIGS. 5A through 5C illustrate proper and improper usage of a single arm walking aid in accordance with a first embodiment. In this example, the user is injured or otherwise has limited immobility on his or her left side (referred to as the weak side). This may be the left foot, leg, hip or lower back or some combination thereof. The relative positions of the left shoe, right shoe and single arm walking aid (e.g. cane or crutch) are shown on the X axis. The time when each item is in contact with the ground is shown as a block during time on the Y axis.

In FIGS. 5A through 5C, time T1 through T10 are based on when the movement of the aid. That is, T1, T5 and T9 are when the aid first touches the ground (strikes). T3 and T7 are when the aid just stopped touching (releases) the ground. The combination of a strike and a subsequent release of the aid is referred to herein as a placement of the aid. The combination of a strike and a subsequent release of a foot is referred to herein as a footstep. The relative timing of footsteps and placement is referred to herein as a gait. Times T1, T3, T5, T7 and T9 can easily be detected by an accelerometer on the aid, thereby indicating the timing of walking aid placements. T2, T4, T6 and T8 are midway between the adjoining strikes or releases. These times can easily be determined based on the average length of time between strikes and releases of the aid.

As the user is walking, there is an overlap of the time one foot strikes and the other foot releases. If there was no overlap, then the user would be running, an improbably event given the user is using an aid such as a cane or crutch.

FIG. 5A illustrates proper usage of a single arm walking aid whereas FIGS. 5B and 5C illustrate common improper usages of a single arm walking aid. The aid placements are shown striking shortly before the left (weak side) foot strikes (T1, T5 and T9) and releasing shortly after the left foot releases (T3 and T7). However, the aid may strike at the same time as the left foot or no later than when the right (strong side) foot releases. The aid may also release at the same time as the left foot or no later than when the right foot strikes. As a result, whenever the left foot is touching the ground, either the right foot or the aid is also touching the ground (T2, T6 and T10).

Also shown in FIG. 5A is the placement of the aid relative to footstep of the left foot. The aid is on the opposite side of the left (weak side) foot next to the right (strong side) foot. This allows for greater balance and safety and a more natural walking posture and gait. If the aid is on the same side of the body as the left foot as shown in FIG. 5B, then the user is leaning to the left without any protection from falling over to the left. In addition, the gait is very unnatural and may cause other issues such as back and shoulder pain or injury.

FIG. 5C illustrates where the aid is used on the correct side of the body, but the user relies on the aid during the time the right (strong side) foot on the ground. As a result, there are periods of time (T2, T6 and T10) where the left (weak side) leg is supporting the full weight of the user, which is inadvisable and may cause further stress and injury.

While FIGS. 5A through 5C are timing diagrams that show the relative location of the right and left feet and aid in the X direction with timing. However, they do not show the relative location of the feet and aid in another (Y) direction although such information is readily discerned from the information provided. For example, in FIGS. 5A and 5B the left foot and aid are sometimes on the ground at the same time as the right foot. However, the left foot and aid are adjoining each other in front of the user while the right foot is behind the user (T1, T5 and T9) or the left foot and aid are adjoining each other behind the user while the right foot is in front of the person (T3 and T7).

Figure 6A:
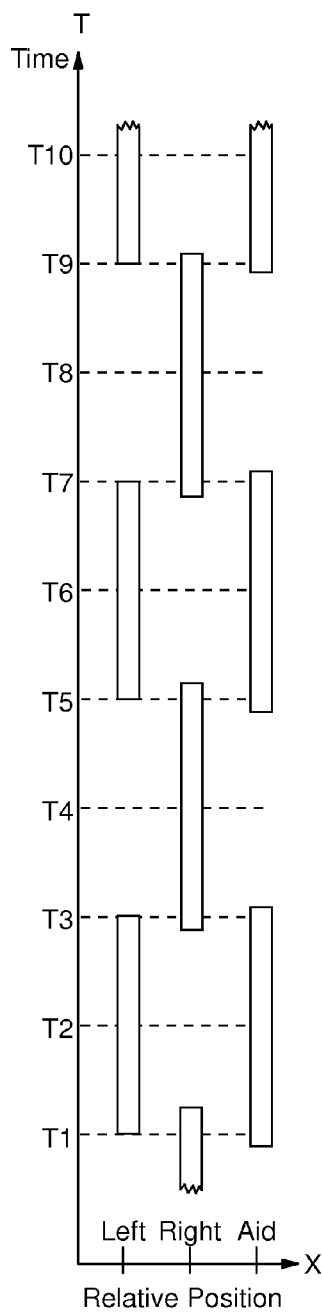
FIG. 6A through 6C illustrate proper and improper usage of a single arm walking aid in accordance with a second embodiment.
Figure 6B:
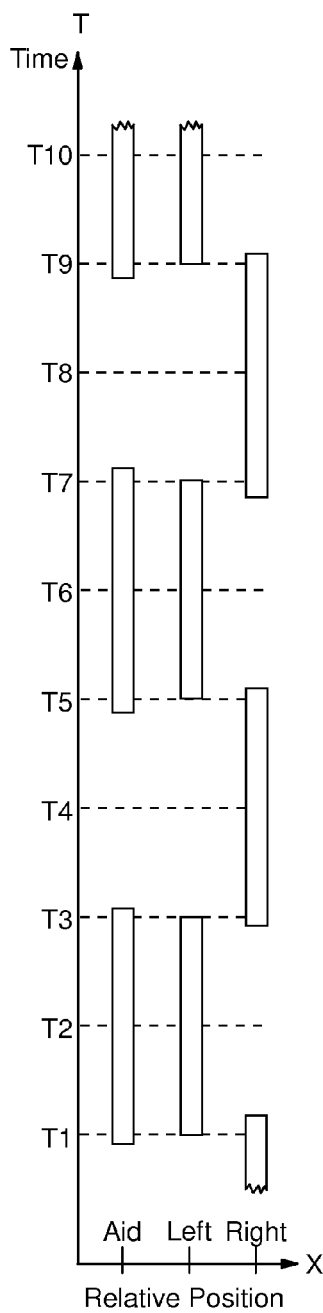
Figure 6C:
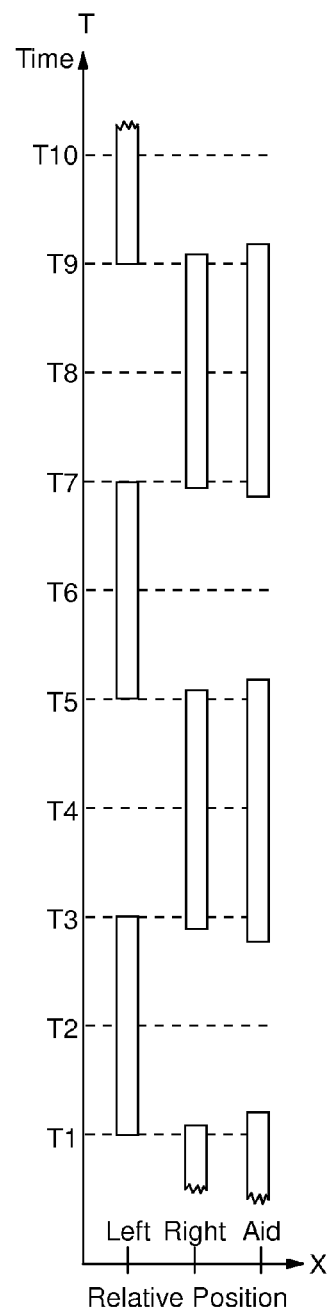

FIGS. 6A through 6C illustrate proper and improper usage of a single arm walking aid in accordance with a second embodiment. In this example, the user is injured or otherwise has limited immobility on his or her left side (referred to as the weak side). This may be the left foot, leg, hip or lower back or some combination thereof. The relative positions of the left shoe, right shoe and single arm walking aid (e.g. cane or crutch) are shown on the X axis. The time when each item is in contact with the ground is shown as a block during time on the Y axis.

In FIGS. 6A through 6C, time T1 through T10 are based on when the movement of the left (mobility impaired) foot. That is, T1, T5 and T9 are when the left foot first touches the ground (strikes). T3 and T7 are when the left foot just stopped touching (releases) the ground. These times can easily be detected by an accelerometer on the left shoe, thereby indicating the timing of the left side footsteps. T2, T4, T6 and T8 are midway between the adjoining strikes or releases. These times can easily be determined based on the average length of time between strikes and releases of the left.

As the user is walking, there is an overlap of the time one foot strikes and the other foot releases. If there was no overlap, then the user would be running, an improbably event given the user is using an aid.

FIG. 6A illustrates proper usage of a single arm walking aid whereas FIGS. 6B and 6C illustrate common improper usages of a single arm walking aid. The left foot (weak side) is shown striking shortly after the aid strikes (T1, T5 and T9) and releasing shortly before the aid releases (T3 and T7). However, the aid may strike at the same time as the left foot or no later than when the right foot releases. The aid may also release at the same time as the left foot or no later than when the right foot strikes. As a result, whenever the left (weak side) foot is touching the ground, either the right (strong side) foot or the aid is also touching the ground (T2, T6 and T10).

Also shown in FIG. 6A is the placement of the aid relative to the footstep of the left foot. The aid is on the opposite side of the left (weak side) foot next to the right (strong side) foot. This allows for greater balance and safety and a more natural walking posture and gait. If the aid is on the same side of the body as the left foot as shown in FIG. 6B, then the user is leaning to the left without any protection from falling over to the left. In addition, the gait is very unnatural and may cause other issues such as back and shoulder pain or injury.

FIG. 6C illustrates where the aid is used on the correct side of the body, but the user relies on the aid during the time the right (strong side) foot on the ground. As a result, there are periods of time (T2, T6 and T10) where the left (weak side) leg is supporting the full weight of the user, which is inadvisable and may cause further stress and injury.

While FIGS. 6A through 6C are timing diagrams that show the relative location of the right and left feet and aid in the X direction. However, they do not show the relative location of the feet and aid in another direction although such information is readily discerned from the information provided. For example, in FIGS. 6A and 6B the left foot and aid are sometimes on the ground at the same time as the right foot. However, the left foot and aid are adjoining each other in front of the user while the right foot is behind the user (T1, T5 and T9) or the left foot and aid are adjoining each other behind the user while the right foot is in front of the person (T3 and T7).

Figure 7:
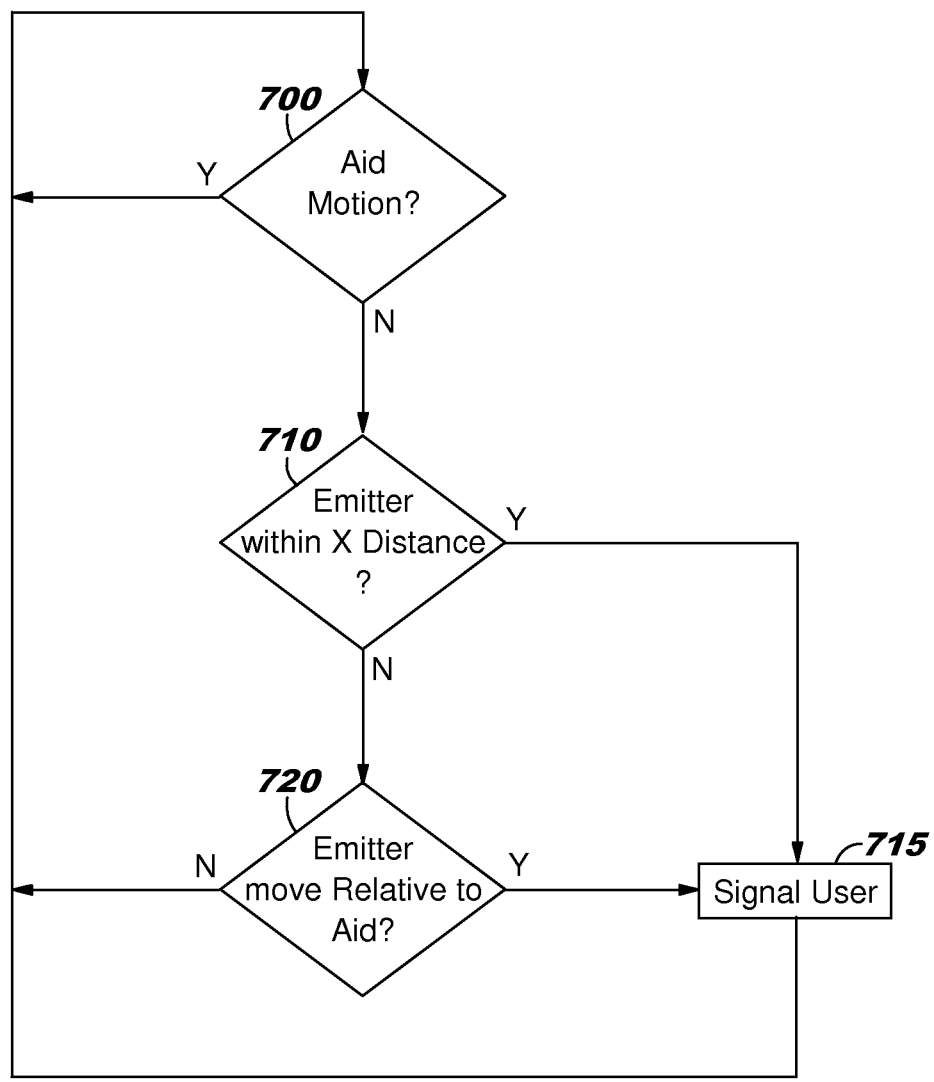
FIG. 7 is a flow diagram of the system for monitoring in accordance with a first embodiment.

FIG. 7 is a flow diagram of the system for monitoring in accordance with a first embodiment. This process identifies improper usage of a single arm walking aid (e.g. a cane or crutch) and signals the user is such improper user is identified.

In this embodiment the only sensor is on the aid for timing input. That is, there is not a sensor on a shoe in this embodiment, so the embodiment will rely on the sensor in the aid to determine when to be checking for proper usage of the aid. A motion detector such as an accelerometer is located on the walking aid to detect when the aid is being moved or not. Alternative embodiments may use other types of motion detectors such as an accelerometer. Additional alternative embodiments may not utilize a motion detector other than a directional proximity detector on the aid and a proximity emitter on the weak side shoe to provide motion, timing, and positional information. In this embodiment, the relative position of the aid to the weak side foot is determined by a proximity detector in the aid and a proximity emitter such as LEDs (light emitting diodes) on the shoe of the injured side. Alternative embodiments may also use proximity emitters on the shoe of the strong side of the user. Other alternative embodiments may use the proximity detector on either the strong side shoe or the weak side shoe with the proximity emitter on the walking aid. Also in this embodiment, there is not a mobile phone or other data processing system coupled to the aid or shoe. In this embodiment, the aid signals to the user through a vibrator in the handle. That is, so long as the aid is properly used, no vibration will be generated or felt by the user. However, if the aid is used improperly, then a vibration is generated and then felt by the user. The aid may be activated by applying pressure to the pressure sensor or by moving the cane such that the movement is detected by the accelerometer.

In a first step 700, the motion sensor such as an accelerometer on the aid is monitored by a processing unit in the aid to determine whether any movement is detected on the foot of the single arm walking aid. If yes, then processing returns to step 700 where it is repeated until no motion is sensed. If no motion is sensed, the in step 710 it is determined whether the weak side shoe is within X inches (or X centimeters depending on the country of use) of the tip of the aid. This is determined by analyzing input from a proximity detector on the tip of the aid and a proximity emitter on the weak side shoe or ankle. The proximity emitter may be as simple as an LED (light emitting diode) attachment to the weak side shoe or ankle. X may be predetermined based on the size of the person, that person's normal gait with an aid, or it may be preset to a certain amount such as 6 inches or 15 centimeters. This will help determine whether the aid is being improperly used for support on the weak side of the user (see FIG. 5B) thereby showing the relative position of the footsteps and placement of the walking aid. If there is an interruption in the signal from the emitter, then this step would assume the proximity emitter is outside an appropriate distance of the proximity detector until determined otherwise. Such an interruption may be caused by the other leg moving in front of the signal from the proximity emitter (see T2, T4, T6, T8 or T10 of FIG. 5A). As a result, if the proximity emitter is within X inches (or centimeters) of the proximity detector the processing continues to step 715. Otherwise, processing continues to step 720. In step 715, the user is signaled that there is an issue with using the aid such as by a vibrator in the handle of the aid. Once the signal to the user is performed, then processing returns to step 700.

In step 720, the processing unit determines whether the weak side foot of the user moves in sequence relative to the aid. That is, it is determined whether the proximity emitter moves in sequence substantially relative to the proximity detector in position, thereby indicating the relative timing of the weak side foot with the aid and by implication the relative placement of the strong side foot relative to the aid. As a result, the relative timing of the footsteps and walking aid placement is determined. If it is determined that the proximity emitter does not move in sequence substantially relative to the proximity detector, then the user is not striking and releasing the aid at about the same time the weak side foot strikes and releases, thereby potentially affecting the gait of the user (see T1, T3, T5, T7 and T9). This could be caused by the user striking the aid at the same time as the strong side foot of the user (see FIG. 5C). A small amount of movement is allowed to avoid false positives as the aid may strike slightly before the foot strikes or the aid may be released slightly after the foot is released. If yes in step 720, then processing returns to step 715 for signaling the user. Otherwise, processing returns to step 700.

In an alternative embodiment, a second proximity emitter could be attached or otherwise incorporated with the strong side shoe. By determining the relative location of the walking aid, the weak side shoe and the strong side shoe, it can be determining whether the cane is being properly used without timing data. That is, by proximity distance and direction alone, you can determine by position alone whether the cane is on the proper side and whether it is being used with the proper foot. For example, if sampled at the time of cane strike, the weak side foot should be closer and either next to or slightly behind the cane whereas the strong side shoe should be behind the weak side shoe. In addition, by comparing the direction of the shoes relative to the cane you can determine whether the cane is on the side of the weak side shoe or not. The same or very similar analysis can be used at the time of cane release. At mid-step, both the cane and weak side shoe should be in the air or on the ground while the strong side shoe should be opposite. In addition, by comparing the direction of the shoes relative to the cane you can determine whether the cane is on the side of the weak side shoe or not. Further analysis of the users gait may need some timing analysis. For example, determining whether the cane strikes the ground before or with the weak side shoe and determining whether the cane releases the ground just after or with the weak side shoe may require timing information. Such timing information may be gleaned from multiple relative positional samples.

Figure 8:
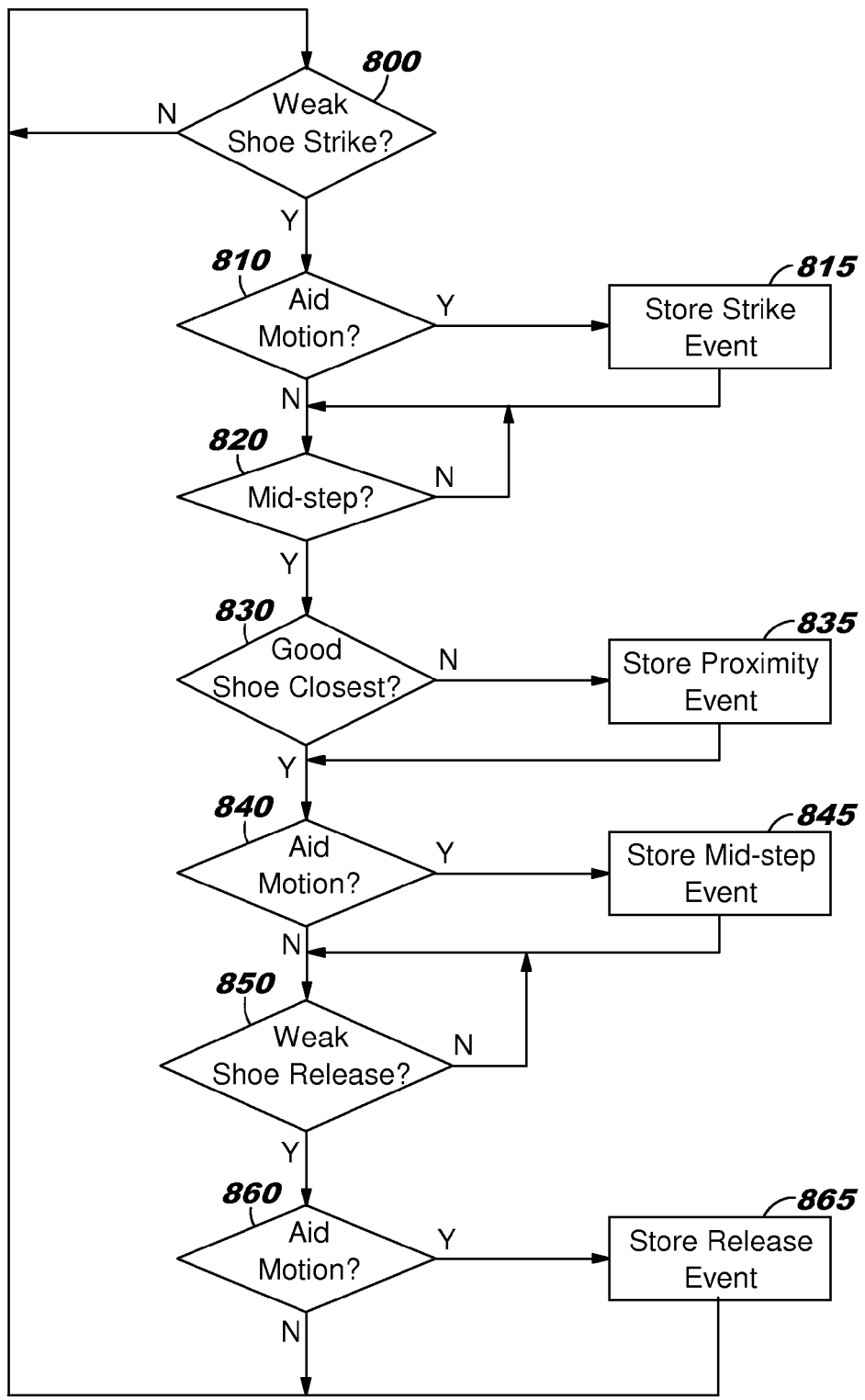
FIG. 8 is a flow diagram of the system for monitoring in accordance with a second embodiment.

FIG. 8 is a flow diagram of the system for monitoring in accordance with a second embodiment. This process identifies improper usage of a single arm walking aid (e.g. a cane or crutch) and signals the user is such improper user is identified.

In this embodiment there are sensors incorporated with both shoes and the aid for motion detection and proximity detection, thereby providing input regarding the relative position and timing of footsteps and walking aid placement. A near field communication device is also included with each sensor to provide communications with a near field communication device in the walking aid. The combination of sensors and detectors in the shoes and walking aid may be collectively referred to as a sensor. Alternative embodiments may use other types of sensors such as an accelerometer or other types of motion detectors to detect when the shoes or aid is being moved or not. In this embodiment, the relative position of the aid to the weak side shoe and the strong side shoe is determined by a proximity detector in the aid and a proximity emitter such as LEDs (light emitting diodes) on both shoes. The proximity emitters use different signals for the weak side shoe and the strong side shoe so the aid may determine which is closer. Alternative embodiments may also use other types of proximity detectors on either or both shoes with an appropriate proximity detector on the aid. The motion sensor, the near field communication device, and the proximity emitter may be a module incorporated with a shoe, either by being built into the shoe or attached to the shoe or ankle of the user. Also in this embodiment, there is a mobile phone or other data processing system coupled to the aid or shoe. The mobile phone may be used for interfacing with the user or a health professional.

In a first step 800, the motion sensor such as an accelerometer on the aid is monitored by a processing unit (located in the mobile phone or the aid) to determine whether any motion is detected on the tip (or handle) of the single arm walking aid. If yes, then processing returns to step 800 where it is repeated until motion is no longer sensed. If no motion is sensed, then the weak side shoe has struck the ground (see T1, T5, T9 of FIG. 6A) and processing proceeds to step 810. In step 810 the processing unit determines whether the aid and strong side shoe are also currently in contact with the ground based on the motion sensor in the aid and the strong side shoe thereby showing the relative timing of the footsteps with the walking aid placement. If not, then processing continues to step 820. If yes, then the aid is not being properly used or the gait of the user may be improper, so in step 815 a strike event is stored to memory. A signal may also be sent to the user or health care professional at the same time. Processing then proceeds to step 820.

In step 820, the processing unit determines whether the user is in mid-step of the weak side (see T2, T6 and T10 of FIG. 6A). This may be determined by timing prior footsteps of the user and calculating a mid-step time. This may also be a preset time after the initial weak side foot strike such as 0.5 seconds. If not, the processing returns to 820 where the step is repeated until the mid-step time occurs. If yes in step 820, then processing continues to step 830. In step 830 the processing unit utilizes the proximity detector to determine whether the strong side shoe is closer to the aid than the weak side shoe. That is, the proximity detector detects the relative location of both feet, thereby showing the relative position of the footsteps and placement of the walking aid. If yes in step 830, then the user is holding the aid on the correct side of his or her body and processing continues to step 840. If no in step 830, then the user is holding the cane on the wrong side of his or her body (see FIG. 6B) and processing continues to step 835. In step 835, a proximity event is stored to memory. A signal may also be sent to the user or health care professional at the same time. Processing then continues to step 840. In step 840 the processing unit determines whether the aid is also currently in contact with the ground (not moving) based on the motion sensor in the aid thereby showing the relative timing of the footsteps with the walking aid placement. If no in step 840, then processing continues to step 850. If yes, then the aid is not being properly used (see FIG. 6C) and in step 845 a mid-step event is stored to memory. A signal may also be sent to the user or health care professional at the same time. Processing then proceeds to step 850.

In step 850, the motion sensor on the aid is monitored by the processing unit to determine whether any motion is detected on the tip (or handle) of the single arm walking aid. If not, then processing returns to step 850 where it is repeated until motion is detected. If a motion is sensed, then the weak side shoe has released the ground (see T3 and T7 of FIG. 6A) and processing proceeds to step 860.

In step 860 the processing unit determines whether the aid and strong side shoe are still in contact with the ground based on the motion sensors in the aid and strong side shoe, thereby showing the relative timing of the footsteps with the walking aid placement. If no, then processing returns to step 800. If yes, then the aid may not be properly used or the gait of the user may be improper, so in step 865 a release event is stored to memory. A signal may also be sent to the user or health care professional at the same time. Processing then returns to step 800.

The various events described above may be accumulated and provided to the user or health care provider for analysis. Based on this analysis, corrective measure may be taken to correct any improper aid usage.

The timings analyzed with this embodiment are the strike, mid-step and release of the weak side shoe. Alternative embodiments may also similarly analyze more point in time with the weak side shoe, the strong side shoe, or the aid. Analysis and feedback may be concurrent with use of the aid or may be performed over time. For example, analysis could show the effects of prolonged use of the walking aid during the day and provide feedback to the user indicating that it is time to rest or to cease walking that day. In addition, analysis could show if the user is experiencing other health issues such as new or increased injury to a side of the body or even identify some of the early signs of a stroke. Additional analysis may be performed such as length of time the user is walking, whether the users gait changes over time (during the day or over a period of days), etc. Additional analysis may also be performed with input from the motion sensors to determine how much weight the user is placing on the weak side foot, the strong side foot and the aid during various parts of a step. This analysis could be shown graphically in comparison to ideal weight distribution profiles. Accelerometer information may also be utilized to determine whether the user in lurching or otherwise moving improperly.

The single arm walking aid may be used in everyday walking by a user or it may be used as a training tool in a health care environment such as a rehabilitation center. Various elements of alternative embodiments may be located in the aid, the shoes or ankles of the user, in a mobile phone or other data processing system, or elsewhere depending on the application and use.

The invention can take the form of an entirely software embodiment, or an embodiment containing both hardware and software elements. In a preferred embodiment, the invention is implemented in software or program code, which includes but is not limited to firmware, resident software, and microcode.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM), or Flash memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Further, a computer storage medium may contain or store a computer-readable program code such that when the computer-readable program code is executed on a computer, the execution of this computer-readable program code causes the computer to transmit another computer-readable program code over a communications link. This communications link may use a medium that is, for example without limitation, physical or wireless.

A data processing system suitable for storing and/or executing program code will include at least one processor coupled directly or indirectly to memory elements through a system bus. The memory elements can include local memory employed during actual execution of the program code, bulk storage media, and cache memories, which provide temporary storage of at least some program code in order to reduce the number of times code must be retrieved from bulk storage media during execution.

A data processing system may act as a server data processing system or a client data processing system. Server and client data processing systems may include data storage media that are computer usable, such as being computer readable. A data storage medium associated with a server data processing system may contain computer usable code such as for monitoring the use of a single arm walking aid. A client data processing system may download that computer usable code, such as for storing on a data storage medium associated with the client data processing system, or for using in the client data processing system. The server data processing system may similarly upload computer usable code from the client data processing system such as a content source. The computer usable code resulting from a computer usable program product embodiment of the illustrative embodiments may be uploaded or downloaded using server and client data processing systems in this manner.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to explain the principles of the invention, the practical application, and to enable others of ordinary skill in the art to understand the invention for various embodiments with various modifications as are suited to the particular use contemplated.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of monitoring single arm walking aid use and gait of a user comprising:
providing a proximity sensor on at least one of a weak side shoe on a weak side foot, a strong side shoe on a strong side foot and a single arm walking aid;
providing a proximity emitter on at least one of the weak side shoe, the strong side shoe and the single arm walking aid;
using the proximity sensor to determine a relative position of a set of footsteps by the weak side foot, a set of footsteps by the strong side foot, and a set of placements of the single arm walking aid based on a relative proximity of the proximity emitter to the proximity sensor; and
using the relative position to determine that the user is practicing incorrect single arm walking aid use when the weak side shoe is within a predetermined distance of the single arm walking aid while the weak side shoe is not moving relative to the single arm walking aid.

2. The method of claim 1 further comprising:
using the proximity sensor to determine a relative timing of the set of footsteps by the weak side foot, the set of footsteps by the strong side foot, and the set of placements of the single arm walking aid based on a relative proximity of the proximity emitter to the proximity sensor over time; and
using the relative timing to determine that the user is practicing incorrect gait with the single arm walking aid when both of the strong side shoe and the single arm walking aid are moving relative to the weak side shoe while the weak side shoe is stationary.

3. The method of claim 2 wherein the sensor comprises:
a single arm walking aid module that includes a proximity detector, a motion detector and a feedback device.

4. The method of claim 2 wherein the sensor comprises:
a foot module incorporated with one of the shoes which contains a first motion detector, a first proximity component and a first near field communication device; and
a single arm walking aid module that contains a second motion detector, a second proximity component and a second near field communication device for communicating with the first near field communication device.

5. The method of claim 4 wherein the sensor further comprises a second foot module incorporated with a second one of the shoes which contains a third motion detector, a third proximity component and a third near field communication device.

6. The method of claim 4 wherein the first proximity component comprises a proximity emitter, and the second proximity component comprises a proximity detector of the proximity emitter.

7. The method of claim 4 wherein the first motion detector is a first accelerometer for determining a strike and release of the shoe and the second motion detector is a second accelerometer for determining a strike and release of the single arm walking aid.

8. The method of claim 4 wherein the single arm walking aid includes a user interface for communicating with the user.

9. The method of claim 8 wherein the user interface comprises a feedback device in the single arm walking aid to indicate improper use of the single arm walking aid.

10. The method of claim 4 further comprising storing a history of the relative timing and position data for analyzing use of the single arm walking device and gait of the user.

11. A computer usable program product comprising a non-transitory computer usable storage medium including computer usable code for use in monitoring single arm walking aid use and gait of a user, the computer usable program product comprising code for performing the steps of:
- communicating with a provided proximity sensor on at least one of a weak side shoe on a weak side foot, a strong side shoe on a strong side foot and a single arm walking aid;
- utilizing a proximity emitter on at least one of the weak side shoe, the strong side shoe and the single arm walking aid;
- using the proximity sensor to determine a relative position of a set of footsteps by the weak side foot, a set of footsteps by the strong side foot, and a set of placements of the single arm walking aid based on a relative proximity of the proximity emitter to the proximity sensor; and
- using the relative position to determine that the user is practicing incorrect single arm walking aid use when the weak side shoe is within a predetermined distance of the single arm walking aid while the weak side shoe is not moving relative to the single arm walking aid.

12. The computer usable program product of claim 11 further comprising:
- using the proximity sensor to determine a relative timing of the set of footsteps by the weak side foot, the set of footsteps by the strong side foot, and the set of placements of the single arm walking aid based on a relative proximity of the proximity emitter to the proximity sensor over time; and
- using the relative timing to determine that the user is practicing incorrect gait with the single arm walking aid when both of the strong side shoe and the single arm walking aid are moving relative to the weak side shoe while the weak side shoe is stationary.

13. The computer usable program product of claim 12 wherein the sensor comprises:
- a single arm walking aid module that includes a proximity detector, a motion detector and a feedback device.

14. The computer usable program product of claim 12 wherein the sensor comprises:
- a foot module incorporated with one of the shoes which contains a first motion detector, a first proximity component and a first near field communication device; and
- a single arm walking aid module that contains a second motion detector, a second proximity component and a second near field communication device for communicating with the first near field communication device.

15. The computer usable program product of claim 14 wherein the sensor further comprises a second foot module incorporated with a second one of the shoes which contains a third motion detector, a third proximity component and a third near field communication device.

16. A data processing system for monitoring single arm walking aid use and gait of a user, the data processing system comprising:
- a processor; and
- a memory storing program instructions which when executed by the processor execute the steps of:
  - providing a proximity sensor on at least one of a weak side shoe on a weak side foot, a strong side shoe on a strong side foot and a single arm walking aid;
  - providing a proximity emitter on at least one of the weak side shoe, the strong side shoe and the single arm walking aid;
  - using the proximity sensor to determine a relative position of a set of footsteps by the weak side foot, a set of footsteps by the strong side foot, and a set of placements of the single arm walking aid based on a relative proximity of the proximity emitter to the proximity sensor; and
  - using the relative position to determine that the user is practicing incorrect single arm walking aid use when the weak side shoe is within a predetermined distance of the single arm walking aid while the weak side shoe is not moving relative to the single arm walking aid.

17. The data processing system of claim 16 further comprising:
- using the proximity sensor to determine a relative timing of the set of footsteps by the weak side foot, the set of footsteps by the strong side foot, and the set of placements of the single arm walking aid based on a relative proximity of the proximity emitter to the proximity sensor over time; and
- using the relative timing to determine that the user is practicing incorrect gait with the single arm walking aid when both of the strong side shoe and the single arm walking aid are moving relative to the weak side shoe while the weak side shoe is stationary.

18. The data processing system of claim 17 wherein the sensor comprises:
- a single arm walking aid module that includes a proximity detector, a motion detector and a feedback device.

19. The data processing system of claim 17 wherein the sensor comprises:
- a foot module incorporated with one of the shoes which contains a first motion detector, a first proximity component and a first near field communication device; and
- a single arm walking aid module that contains a second motion detector, a second proximity component and a second near field communication device for communicating with the first near field communication device.

20. The data processing system of claim 19 wherein the sensor further comprises a second foot module incorporated with a second one of the shoes which contains a third motion detector, a third proximity component and a third near field communication device.

* * * * *